United States Patent [19]

Tickner et al.

[11] 4,276,885

[45] Jul. 7, 1981

[54] ULTRASONIC IMAGE ENHANCEMENT

[75] Inventors: Ernest G. Tickner, Morgan Hill; Ned S. Rasor, Santa Clara County, both of Calif.

[73] Assignee: Rasor Associates, Inc, Sunnyvale, Calif.

[21] Appl. No.: 36,098

[22] Filed: May 4, 1979

[51] Int. Cl.$^3$ ............................................. A61B 10/00
[52] U.S. Cl. .................................................... 128/660
[58] Field of Search ............................... 128/660–663, 128/861.41; 73/194 A

[56] References Cited

U.S. PATENT DOCUMENTS

| 3,640,271 | 2/1972 | Horton | 128/662 |
| 4,182,173 | 1/1980 | Papadofrangakis et al. | 73/194 A |

OTHER PUBLICATIONS

Yang, W. et al., "Exper. Studies of Dissolution of Gas Bubbles in Whole Blood & Plasma 14 I. Stationary Bubbles", Jrnl. Biomech. vol. 4 pp. 275–281 1971.
Gramiak, R. et al., "Detection of Intra-Cardiac Blood Flow by Pulsed Echo-Ranging Ultrasound", Radiology vol. 100, Aug. 1971 pp. 415–418.
Feigenbaum, H. et al., "Identification of UTS Echoes from the Left Ventricle by Use of Intracardiac Injections of Indocyanine Green", Circulation Vol. XLI, Apr.1970 pp. 614–621.
"Gelatin" Publ. of Gelaltin Mnfctrs. Inst. of Amer. Inc., 55 West 42nd Street, New York, N.Y.
Lubbers, J. et al. "An Ultrasonic Detector for Micro Gas Emboli in a Blood Flow Line ", UTS in Med & Biol., No. 4 1977 pp. 301–310.
Peronneau, P. et al., "Real-Time Measurement of Blood Velocity Profiles by UTS Multi-gated Pulsed Doppler Velocimeter", Conf. Digest 3rd Intnl. Conf. on Med. Physics, Chalmers Univ. of Tech. Göteberg Sweden 1972.
Maywald, G. "Experience with Atraumatic Vascular Diagnosis with the Aid of the UTS Doppler Technique", Electromedica No. 2 pp. 43–48, 1976.
Fairbank, W. M. et at., "A New Non-Invasive Technique for Cardiac Pressure Measurement: Resonant Scattering of Ultrasound from Bubbles", IEEE Trans. on Biomed. Engr. vol. BME-24,No. 2 Mar. 1977 pp. 107–110.
Tickner, E. G. et al., "Non-Invasive Assessment of Pulmonary Hypertension Using the Bubble UTS Resonance Pressure (BURP) Method", Report No. HR-629-17-1A Prepared for Natnl. Hrt., Lung and Blood Inst., Bethesda, Md. Apr. 1977.

*Primary Examiner*—Henry J. Recla
*Assistant Examiner*—Francis J. Jaworski
*Attorney, Agent, or Firm*—Phillips, Moore, Weissenberger Lempio & Majestic

[57] ABSTRACT

Ultrasonic images of flowing streams can provide important information regarding the streams. Herein, a plurality of microbubbles are provided in such streams to enhance such images, aid in tumor detection and treatment, provide mapping of vascularity of tissue masses and measure instantaneous blood flow rate. The preferred microbubbles have a coalescence resistant surface membrane encapsulating a gas of a selected composition, the membrane including non-toxic and non-antigenic organic molecules. Preferably, the microbubbles have diameters in the 0.5 micron-300 micron range.

15 Claims, No Drawings

ULTRASONIC IMAGE ENHANCEMENT

DESCRIPTION

1. Technical Field

This invention relates to an ultrasonic image enhancement method, to diagnostic techniques and to treatment methods which are closely related thereto.

2. Background Art

Contrast agents are often employed medically to accentuate subtle differences between two structures in X-ray radiographic images. In X-ray diagnosis, for example, a radioopaque dye is routinely injected into an arterial bed to delineate the existing vasculature which otherwise could not be detected. Present ultrasonic diagnosis generally faces similar problems. The ultrasonographer has comparable difficulty in detecting certain structures, for example septal defects in small children, but no effective ultrasonic contrast agent has been available. An acceptable ultrasonic contrast agent which can be delivered into the blood stream therefore is greatly needed. A selective agent, i.e., one which can selectively emphasize particular parts of the vasculature (such as that of a tumor), would be especially valuable.

Measurement of cardiac output and other quantitative blood flow measurements are needed to monitor the health of many patients. Existing non-invasive measurement techniques are indirect and only approximate. Existing reliable and accurate measurement techniques involve catheterization, a difficult and hazardous procedure. Further, the prior art does not yield a measurement of instantaneous blood flow, but only an average value thereof. An accurate non-invasive method for measurement of cardiac output and blood flow in general is greatly needed.

Feigenbaum, et al, Circulation, Volume XLI, April 1970, in a report titled "Identification of Ultrasound Echoes From the Left Ventricle of the Heart Through the Use of Injections of Indocyanine Green" noted that injections of the indocyanine green produced a cloud of echoes that filled the left ventricle cavity. They speculated that this phenomenon might be due to the formation of tiny bubbles of air suspended in the dye. Gramiak, et al, Radiology 100:415–418, 1971, report similar effects.

Although some enchoing has been noted and presumed to be caused by microbubbles in the blood stream, the hypothesis that the microbubbles cause the echoing has never been conclusively proven. Further, the proir results in this area have been on a hit-or-miss basis, in that the bubbles introduced into the blood stream, if indeed they were bubbles, have been of generally uncontrolled and unstable size and concentration.

Still further, when the bubbles are simply air bubbles, they have a serious and deleterious tendency to stick to the vessel and cardiac walls and to coalesce and form larger bubbles. Hence, it has not been possible to introduce bubbles that are of relatively uniform size into blood vessels, which bubbles resist coalescence, flow freely with the blood and remain of a relatively uniform size as they dissolve. Thus, diagnostic techniques which might depend upon having freely flowing microbubbles of a controlled size in the blood stream, and in a controlled amount, have not been developed and do not form a part of the ultrasonic diagnostic art.

The production of freely flowing microbubbles of a controlled size and their injection into the blood stream for different diagnostic techniques is known. The present inventors, in a report entitled "Non-Invasive Assessment of Pulmonary Hypertension Using The Bubble Ultrasonic Resonance Pressure (BURP) Method" (Report No. HR-62917-1A), April, 1977 sponsored by the Division of Lung Diseases, National Heart, Lung and Blood Institute, report on the production and the attempt to use such bubbles for non-invasively measuring pulmonary artery blood pressure by sensing bubble ultrasonic resonance. Basically, microbubbles are injected into a peripheral vein and their ultrasonic resonance re-emission frequency is measured as they pass through the pulmonary artery. The re-emission resonance frequency (about 100 kHz or less) is determined by applying an ultrasonic probe to the chest of the subject. The bubbles are excited by transmission of continuous ultrasonic radiation (of about 100 kHz) into the body. The microbubbles are not, however, utilized by the prior art for enhancing ultrasonic images. That is, they are not used at mega-Hertz frequencies, e.g., 1 to 10 mega-Hertz, and are not used via applying short ultrasonic pulse and detecting timed echoes therefrom as with ultrasonic echograms, or via applying continuous waves and examining the changes in transmission characteristics as with existing ultrasonic holographic units.

It would be highly desirable to provide a method of controllably and uniformly enhancing ultrasonic images of the blood stream of a living subject. Such a method could be utilized, for example, for detecting tumors and other abnormalities, for measuring instantaneous cardiac output and flow velocities in other vessels, for delivering gaseous therapeutic agents selectively to tumors or other tissues, and the like.

DISCLOSURE OF INVENTION

The present invention is directed toward overcoming one or more of the shortcomings of the prior art as set forth above.

According to the present invention, a method is set out for enhancing ultrasonic images of the blood stream of a patient. The method comprises flowing a plurality of microbubbles, each having a surface membrane encapsulating a gas of a selected composition, the membrane including a multiplicity of non-toxic and non-antigenic organic molecules, the microbubbles each having a diameter of no more than about 300 microns and no less than about 0.5 microns, in the blood stream; obtaining ultrasonic images of the blood stream opposite a position therein through which the microbubbles are flowing, thereby rendering the blood-carrying vessel visible by virtue of the increased contrast of the blood stream from the surrounding tissue, and permitting detection of abnormalities in configuration or function of the vessel.

In another sense, the invention comprises a method of measuring instantaneous flow in blood vessels including cardiac output. The method comprises injecting a substance into a blood stream of a test subject, the substance providing an ensemble of microbubbles; measuring the instantaneous velocities of the microbubbles at a location in the blood stream by substantially simultaneously measuring the time dependent positions of the ensemble of microbubbles across the diameter of the vessel at said location; and determining therefrom the substantially instantaneous volumetric flow rate at the location in the blood stream.

In still another sense, the invention relates to a method of detecting tumors in a living subject. The method comprises injecting a substance into a blood stream of the subject, the substance providing a plurality of controlled size microbubbles in the blood stream; obtaining an ultrasonic image of the bubbles; and examining the image for evidences of neovascularization, with or without a necrotic core, indicative of a possible tumor.

Still further, in another embodiment of the invention, a method is provided of delivering a gaseous therapeutic agent selectively to tumorous tissue. The method comprises injecting such microbubbles as have been previously discussed, wherein the gas therein comprises a therapeutic agent.

In yet another sense, the invention comprises a method of measuring the afferent vascularity of a certain tissue mass. The method comprises injecting or infusing a substance providing a plurality of precision microbubbles. The bubble diameter is preselected for the dimension of concern. The microbubbles flow into the general area for ultrasonic examination and lodge at a bifurcation whose discharge branches are all smaller than the bubble. The ultrasonic images thereby show areas of similar bifurcation sizes. As the bubbles dissolve, they become free and flow downstream and lodge at another bifurcation. Coupled with knowledge of bubble dissolving rates, time-sequenced images can delineate the afferent vascularity of the test section.

To summarize, the present invention concerns an injectable stable dispersion of microbubbles of precisely controllable size and quantity for use as an effective and safe contrast agent for ultrasonic imaging, and for direct non-invasive measurement of cardiac output and blood flow in general. The size control is important in that it adds a dimension of diagnostic uses not available with X-ray contrast agents. The invention also concerns delivery of a gaseous therapeutic agent selectively to tumorous tissue.

BEST MODE FOR CARRYING OUT THE INVENTION

In accordance with the present invention ultrasonic images of a blood stream of a subject are enhanced. Either via catheterization injection or through hypodermic injection, a plurality of microbubbles of a very particular nature are inserted into the blood stream of the test subject. The microbubbles must each have a surface membrane which encapsulates a gas of a selected composition.

The structure of the membrane is of extreme importance. It should be selected to reduce coalescence and must include a multiplicity of non-toxic and non-antigenic organic molecules. Gelatin is particularly preferred as the membrane material. The organic molecules which form a gelatin membrane are believed to have both a hydrophilic portion and a hydrophobic portion. When the membrane-covered microbubbles are in the blood stream, the hydrophilic portions are believed to be aligned radially outwardly or away from the centers of the respective microbubbles. As a result, the microbubbles tend to repel one another thus significantly reducing the tendency of the microbubbles to coalesce with one another and form larger microbubbles.

Membranes other than gelatin and having resistance to coalescing, as well as non-toxic and non-antigenic properties, are also suitable whether the resistance to coalescing is due to the presence of such hydrophilic and hydrophobic portions, to particularly strong membranes, or whatever. This resistance to coalescing is important in ensuring that the sizes of the microbubbles in the blood stream are substantially the same for microbubbles which are originally of the same size and have been in the blood stream an equal length of time. With time, of course, the gas or gases contained within the membranes will dissolve into the blood stream and the microbubbles will be gradually reduced in size until they disappear.

It is essential that the organic molecules which form the membrane be non-toxic and non-antigenic, since it is clear that either a toxic or antigenic reaction within the blood stream is highly undesirable.

With respect to the gas within the membrane, for straightforward ultrasonic image enhancement, a chemically inert and somewhat slowly dissolving gas such as nitrogen or one of the slower dissolving noble gases is very suitable. However, in certain instances it may be desirable to utilize a gas which is far from inert. For example, it may be desirable to utilize a gas within the bubble which is toxic to tissue, if the bubble is designed to be absorbed by tumorous tissue but to not be absorbed by the normal tissue of the blood stream. In other instances, it may be desirable to employ a gas which dissolves in blood quickly, such as carbon dioxide.

Another important result of utilizing microbubbles having the particular membrane described above is that they will have a reduced tendency to stick to the walls of the blood vessel, particularly the walls of normal blood vessels. With tumorous tissue, the walls of the blood vessels are considerably rougher and otherwise abnormal, thus providing a more ready accepting surface for holding such microbubbles, even with their reduced tendency to stick to normal blood vessel walls.

The size of such microbubbles is also important. Generally they will be, at most, about 300 microns, and at least about 0.5 micron, in diameter. More preferably, the microbubbles will have a diameter below about 150 microns and above about 1.0 micron. In some instances, all of the microbubbles injected will be of about the same size so that they congregate in a particular area of the body or in a particular type or size of blood vessel. Microbubbles between 5 and 10 microns are particularly useful in that they can pass through normal capillaries.

Such microbubbles as have just been described are produced by gradually flowing a gas through a small orifice, for example through a capillary tube, and into a liquid. A force is generally exerted upon the microbubble being formed at the orifice, with the force being sufficient to remove the microbubble prior to its attaining the full size it would attain in the absence of such force. For example, the orifice may lie generally in a vertical plane (the capillary may be horizontal) and the force may simply comprise the buoyancy of the microbubble in the liquid and the surface tension attachment to the orifice. Alternatively, and preferably, the orifice may lie in any orientation with flow past the orifice, and the force consists of fluid drag on the bubble and the surface tension force. In both situations the microbubbles may flow into a storage container such as a hypodermic syringe. The aforementioned report "Non-Invasive Assessment of Pulmonary Hypertension Using The Bubble Ultrasonic Resonance Pressure (BURP)

Method" describes production of such microbubbles in more detail.

Other methods of producing the described microbubbles have been successfully employed. For example, microbubbles have been created by supersaturation of a liquid; air or liquid jet impingment upon a free liquid surface; and addition of $NaHCO_3$ particles to a liquid. These latter methods permit production of large quantities of microbubbles but of a much broader spectrum of sizes than the highly uniform diameter of microbubbles produced by a submerged orifice.

It is preferred that the microbubbles be formed and dispersed in a medium having a chemical composition substantially identical to that of the membrane. It is further preferred that the medium be gellable. As previously mentioned, a particularly preferred membrane material is gelatin itself, because it is well known to be non-toxic, non-antigenic and non-allergenic. Utilizing a gellable medium allows the microbubble dispersion to be stored for extended periods of time by simply lowering the temperature of the medium sufficiently so that gelling occurs. In practice, the gelled microbubble dispersion is stored in hypodermic syringes. When needed, the gelatin is melted by warming the syringes, and the dispersion is injected into a blood vessel. The bulk of the gelatin dissolves in the blood, leaving the required gelatin stabilizing membrane around each microbubble.

As the microbubbles flow through the blood stream, ultrasonic images are obtained of the blood stream opposite a location therein through which the microbubbles are flowing. Most modern clinical ultrasonic units employ pulsed ultrasound to obtain images within the body. A short burst of ultrasound is emitted from the exciter/receiver transducer into the test media. Slight changes in acoustical impedance cause some reflection of the incident pulse train. The intensity of the reflection received by the transducer is a function of the difference between the acoustical impedance of the two media forming the interface. The time to acquire the return signal depends upon the distance travelled. Signal and video processing leads to an echogram of the test media, and the brightness of an interface depends upon the strength of the reflection. Use of the ultrasonic echogram technique along with a microbubble contrast medium is identical to that normally utilized. That is, no variations in the ultrasonic imaging device itself are necessary.

It should be noted that the particular size of the microbubbles may be optimized in relation to the frequency of the ultrasound being utilized to obtain the image. That is, for a highly reflecting dispersion, the size of the microbubbles can be chosen so that they resonate at the particular ultrasonic frequency utilized, although at the most used imaging frequencies, 2 to 10 mHz, this may require microbubbles having very small (1 to 5 micron) diameters. The reflection power of the bubbles at resonance can be more than 100 times that at non-resonance frequencies.

Instantaneous cardiac output can be measured utilizing microbubbles injected into the blood stream. The blood flow velocity distribution in a blood vessel or heart chamber can be quantitatively determined by the use of injected microbubbles, provided that the bubbles which reach the observed location are of suitable number and size for discrete and accurate measurement of their position in the ultrasonic image. The velocity distribution is obtainable by either one of two methods. The first method is to observe the local displacement of the bubbles throughout the vessel or chamber over a short increment of time. This is conveniently accomplished in the usual ultrasonic image by measuring the bubble "streak length", i.e., the change in position of each bubble between successive ultrasonic scans. The second method is to detect the Doppler shift frequency from the backscattered signal from each bubble. A three-dimensional velocity field can be determined stereoscopically using images from different aspects (angles). Such instantaneous distributions can reveal the presence and quantitative severity of flow abnormalities such as septal defects and valvular disfunctions in the heart, and obstructions or aneurysms in the coronary, aorta, carotid and other vital blood vessels. Furthermore, by integrating the velocity profile across the diameter of a great vessel of the heart such as the pulmonary artery or the ascending aorta, a direct measurement of instantaneous cardiac output can be obtained non-invasively. This important measurement previously could be obtained only by catheterization, a difficult and hazardous procedure, or by inaccurate and ambiguous indirect methods, and as averages over the cardiac cycle rather than instantaneous values.

Tumors can be detected in a living test subject via ultrasonic images by observing the abnormal concentration of microbubbles in an area where a tumor is suspected. Basically, the vasculature of a tumor grows at a rapid rate and becomes erratic and larger than that of normal tissue. Because the neovascularized vessels are larger than normal vessels, increased blood flow exists and a much higher concentration of microbubbles will be present. In particular, if microbubbles of a particularly appropriate size are chosen, it is possible to selectively collect such microbubbles within the tumor neovasculature and to thus delineate the extent of the neovascularity with a quantitative image. Alternatively, by using microbubbles of a uniform size larger than the normal capillary diameter, i.e., 7 to 10 microns, but well within the range of abnormal tumor capillary diameter, i.e., 20 to 100 microns, the local presence of the tumor is unambiguously identified by microbubbles which pass through the afferent vasculature and appear in the efferent (venous) vasculature.

EXAMPLE

The following example illustrates the use of microbubbles as ultrasonic contrast agents.

Nitrogen microbubbles (38, 80 and 140 microns in diameter) dispersed in gelatin, were injected via a catheter into test subjects. Static (5 mHz transducer) and real time (7.5 mHz transducer) images were recorded on Polaroid film and on videotape. Rabbits with unilateral thigh V2 carcinomas were used in the in vivo studies. Base-line ultrasound images of normal muscle and V2 carcinoma were obtained. Five milliliter syringes containing a gelatin dispersion of 80 micron nitrogen microbubbles were warmed and injected through a catheter placed in the V2 ipsilateral iliac artery via the right carotid artery. Static and real time images of normal muscle, blood vessels, and the V2 carcinoma, which was located by palpation, were recorded for at least 2 minutes following each injection. The gelation-encapsulated nitrogen bubbles were also readily demonstrated in an in vitro phantom. The 80 and 140 micron bubbles were more echogenic than the 38 micron bubbles, although this may be a result of the instrumentation and geometry of the test. In vivo, the 80 micron microbubbles could be identified for several minutes after the initial bolus of bubbles. The central anechoic portions of the V2 carcinoma did not become echogenic following injection of microbubbles but the periphery of the tumor became increasingly echogenic. The gelatin-encapsulated nitrogen microbubbles are thus demonstrated as being an effective ultrasonic contrast agent. The ultrasonic tumor rim enchancement about a necrotic core was found to be a useful diagnostic observation.

The tumor detection technique just discussed and exemplified can be modified to serve as a tumor treatment technique. That is, the gas encapsulated within the membrane can be changed to one which will deliver radioactive or chemotherapeutic agents to the tumor neovascularization. It is noted that such is in conformance with the exemplified concentrating of microbubbles in the neovascularized tumor tissue and with the selectively large dissolution rate of the bubbles in the capillary bed.

INDUSTRIAL APPLICABILITY

The aforementioned and described methods are useful diagnostically for a number of purposes, including but not limited to the detection of cardiovascular abnormalities and tumors in living beings, and the selective local delivery of therapeutic agents. Still further, the method is useful in providing a direct and non-invasive measurement of instantaneous cardiac output and blood flow in general, whereas it was previously not possible to make such an instantaneous measurement, but rather only to measure average cardiac output or blood flow by invasive or indirect procedures.

Other aspects, objects, and advantages of this invention can be obtained from a study of the drawings, disclosure and the appended claims.

We claim:

1. A method of enhancing ultrasonic echographic imaging in a liquid enclosed in a vessel by increasing image contrast, comprising:
   providing a plurality of microbubbles in said liquid, each of said microbubbles having a coalescence resistant surface membrane encapsulating a gas of a selected composition, said membrane including a multiplicity of non-toxic and non-antigenic organic molecules, said microbubbles having a diameter of no more than about 300 microns and no less than about 0.5 micron; and
   obtaining an enhanced ultrasonic echographic image of said liquid opposite a position therein containing said microbubbles by increasing the relative contrast between said liquid and said vessel.

2. A method as in claim 1, wherein said liquid is a blood stream of a test subject.

3. A method as in claim 1, wherein said molecules each have a hydrophilic portion and a hydrophobic portion and said hydrophilic portions of said molecules are aligned radially away from a center of a respective microbubble.

4. A method as in claim 1, wherein said membrane is of a gellable composition.

5. A method as in claim 4, wherein said gellable composition is gelatin.

6. A method of detecting tumors in a living subject, comprising:
   providing a substance in a blood stream of said test subject, said substance providing a plurality of microbubbles in said blood stream, substantially all of said microbubbles being of generally a uniform size;
   obtaining an enhanced ultrasonic echographic image of said bubbles at a possible tumor; and
   examining said image for evidence of neovascularization indicative of said possible tumor.

7. A method of detecting tumors in a living subject, comprising:
   providing a substance, comprising a plurality of microbubbles each having a surface membrane encapsulating a gas of a selected composition, said membrane including a multiplicity of non-toxic and non-antigenic organic molecules, in a blood stream of said test subject, said substance providing a plurality of microbubbles in said blood stream;
   obtaining an enhanced ultrasonic echographic image of said bubbles; and
   examining said image for evidence of neovascularization indicative of a possible tumor.

8. A method as in claim 7, wherein said molecules each have a hydrophilic portion and a hydrophobic portion, said hydrophilic portions of said molecules being aligned radially away from a center of each respective bubble, said microbubbles are of generally a uniform size and of a diameter of no more than about 300 microns and no less than about 0.5 micron.

9. A method as in claim 7, wherein said membrane is of a gellable composition.

10. A method as in claim 7, wherein said membrane comprises gelatin.

11. A method of mapping the vascularity of a tissue mass, comprising:
   injecting a plurality of microbubbles, substantially all of which fall in a selected narrow size range, into a blood stream of a test subject, each of said microbubbles having a coalescing resistant surface membrane encapsulating a gas of a selected composition, said membrane including a multiplicity of non-toxic and non-antigenic organic molecules, said molecules having a diameter of between about 0.5 micron and 300 microns;
   obtaining an enhanced ultrasonic echographic image of the tissue mass soon after the microbubbles have flowed thereto and lodged at a first bifurcation of a first vascular size corresponding to that of the injected microbubble size range; and
   obtaining an additional enhanced ultrasonic echographic image of the tissue mass after a selected period of time during which the microbubbles have generally uniformly shrunk, due to dissolution thereof, to a known reduced size, have flowed past said first bifurcation, and have lodged at a second bifurcation of a second vascular size corresponding to that of the reduced size microbubble size range.

12. A method as in claim 11, wherein said organic molecules each have a hydrophilic portion and a hydrophobic portion, said hydrophilic portions of said molecules being aligned radially away from a center of each respective microbubble.

13. A method as in claim 11, wherein said membrane is of a gellable composition.

14. A method as in claim 13, wherein said gellable composition is gelatin.

15. A method of detecting tumorous tissue in a living subject, comprising:
   providing a substance in an afferent vasculature of said test subject upstream of a possible tumor, said substance providing a plurality of microbubbles in said blood stream substantially all of a diameter too large to pass through normal capillaries but small enough to pass through tumorous capillaries; and
   obtaining an enhanced ultrasonic echographic image of a corresponding efferent vasculature downstream of said possible tumor and noting if such microbubbles are present.

* * * * *